United States Patent
Cheng et al.

(10) Patent No.: US 11,383,090 B2
(45) Date of Patent: Jul. 12, 2022

(54) PACE-MAKING FIXING SYSTEM, LEAD-FREE PACEMAKER SYSTEM, AND USE METHOD THEREFOR

(71) Applicant: MICROPORT SOARING CRM (SHANGHAI) CO., LTD., Shanghai (CN)

(72) Inventors: Zhijun Cheng, Shanghai (CN); Grace Ying Yang Jang, Shanghai (CN); Li Wang, Shanghai (CN); Jiangkai Sun, Shanghai (CN)

(73) Assignee: MICROPORT SOARING CRM (SHANGHAI) CO., LTD., Shanghai (CN)

(*) Notice: Subject to any disclaimer, the term of this patent is extended or adjusted under 35 U.S.C. 154(b) by 126 days.

(21) Appl. No.: 16/650,738

(22) PCT Filed: Sep. 25, 2018

(86) PCT No.: PCT/CN2018/107398
§ 371 (c)(1),
(2) Date: Mar. 25, 2020

(87) PCT Pub. No.: WO2019/057213
PCT Pub. Date: Mar. 28, 2019

(65) Prior Publication Data
US 2020/0306551 A1    Oct. 1, 2020

(30) Foreign Application Priority Data
Sep. 25, 2017   (CN) .......................... 201710875812.4

(51) Int. Cl.
*A61N 1/375*   (2006.01)
*A61N 1/372*   (2006.01)

(52) U.S. Cl.
CPC ....... *A61N 1/37518* (2017.08); *A61N 1/3756* (2013.01); *A61N 1/37205* (2013.01); *A61N 1/37512* (2017.08); *A61N 1/37516* (2017.08)

(58) Field of Classification Search
CPC ............ A61N 1/37518; A61N 1/37205; A61N 1/37516; A61N 1/37512; A61N 1/3756; A61N 1/057
See application file for complete search history.

(56) References Cited

U.S. PATENT DOCUMENTS

| 4,798,206 A | 1/1989 | Maddison et al. |
| 8,527,068 B2 | 9/2013 | Ostroff |

(Continued)

FOREIGN PATENT DOCUMENTS

| CN | 103328040 A | 9/2013 |
| CN | 103381284 A | 11/2013 |

(Continued)

OTHER PUBLICATIONS

International Search Report and Written Opinion (with English translations) dated Nov. 16, 2018 issued in corresponding Application No. PCT/CN2018/107398.

*Primary Examiner* — Eugene T Wu
(74) *Attorney, Agent, or Firm* — Muncy, Geissler, Olds & Lowe, P.C.

(57) ABSTRACT

A pacemaker fixation system, a leadless pacemaker system and a method of use thereof are disclosed. The leadless pacemaker system includes: a pacemaker fixation system including a leadless pacemaker and an elastic unfoldable element attached thereto, wherein in an unfolded configuration of the elastic unfoldable element, it fixes the leadless pacemaker at a target location in a blood vessel in communication with the heart; a delivery system for delivering the pacemaker fixation system to the target location; and a guide for guiding the delivery system into the blood vessel.

(Continued)

According to the present invention, atrial pacing can be achieved by the leadless pacemaker through fixing the leadless pacemaker in the blood vessel in communication with the heart with the elastic unfoldable element.

19 Claims, 9 Drawing Sheets

(56) References Cited

U.S. PATENT DOCUMENTS

| | | | |
|---|---|---|---|
| 9,775,991 B1* | 10/2017 | Hakki | A61N 1/362 |
| 2005/0228471 A1 | 10/2005 | Williams et al. | |
| 2009/0281521 A1* | 11/2009 | Williams | A61N 1/37518 |
| | | | 604/509 |
| 2011/0238077 A1 | 9/2011 | Wenger | |
| 2012/0172891 A1* | 7/2012 | Lee | A61N 1/3756 |
| | | | 606/129 |
| 2013/0253309 A1* | 9/2013 | Allan | A61B 5/0031 |
| | | | 600/424 |

FOREIGN PATENT DOCUMENTS

| | | |
|---|---|---|
| CN | 105916544 A | 8/2016 |
| CN | 106178262 A | 12/2016 |
| CN | 106362288 A | 2/2017 |
| CN | 107583187 A | 1/2018 |
| WO | WO 2017/106693 A1 | 6/2017 |

\* cited by examiner

PACE-MAKING FIXING SYSTEM, LEAD-FREE PACEMAKER SYSTEM, AND USE METHOD THEREFOR

TECHNICAL FIELD

The present invention relates to implantable cardiac pacemaker systems and, in particular, a pacemaker fixation system, a leadless pacemaker system and a method of use thereof.

BACKGROUND

Since the advent in 1958, cardiac pacemakers have become a first-line treatment for bradycardia arrhythmia. With the advancements and innovations over the past more than half century, pacemakers have gradually evolved from the initial form of single leads for open chest implantation and ventricular pacing to the recent form of 2-3 leads for intravenous implantation and atrioventricular physiological pacing or even biventricular synchronous pacing. Nevertheless, lead removal remains difficult and risky and must be performed in large electrophysiology centers by highly skilled surgeons. Lead-related complications such as lead dislodgement, thrombosis, tricuspid regurgitation and infection can not only interrupt the normal operation of pacemakers but can seriously threaten patients' health and lives and degrade their quality of life. Now, how to break through the bondage of lead and thus bring about a "leadless" revolution is a new direction in the field of arrhythmia treatment.

Application No. 201180061312.8, entitled "Leadless Pacemaker with Radial Fixation Mechanism" provides a leadless cardiac pacemaker with a radial fixation mechanism. The cardiac pacemaker includes a radial fixation mechanism that is separate from a pacing electrode and the radial fixation mechanism has a diameter equal to or smaller than an outer diameter of the pacemaker. The fixation mechanism allows the pacemaker to be inserted into tissue with 2 rotations of the pacemaker to contact the tissue to fix the pacing electrode. In some embodiments of the application, the fixation mechanism can include a plurality of hooks or protrusions positioned near a distal (distal from the operator) portion of the pacemaker. One or more of such fixation mechanisms can be configured to penetrate the endocardium of the patient and reside mostly within the myocardium. The application also provides methods of delivering the leadless cardiac pacemaker into the heart.

Application Publication U.S. Pat. No. 8,527,068 B2 provides a leadless pacemaker with double fixation capabilities, in which a circular ring-shaped feature is provided at a proximal (close to the operator) end of the leadless pacemaker. This structure allows the leadless pacemaker to stop within the right ventricle upon the failure of its distal fixation mechanism, preventing its entry into the blood circulation system, which may endanger the patient.

In both these proposed solutions, the pacemaker is delivered to the right ventricular apex by a delivery system and then rotated so that a helical feature at a distal end thereof screws into the relative thick apical myocardial tissue. However, fixation of such a leadless pacemaker relying on the screwing action of the helical feature to the atrial wall that is very thin will be associated with severe hazards such as insecure fixation, atrial perforation, etc. For this reason, both the conventional leadless pacemakers are only suitable for univentricular pacing but not for the traditional biventricular or cardiac resynchronization therapy pacing, possibly leading to non-physiological pacing with atrioventricular desynchronization and limiting the population that can indeed benefit from the leadless pacing technology typically only to those with chronic atrial fibrillation or elders.

SUMMARY OF THE INVENTION

The present invention provides a pacemaker fixation system, a leadless pacemaker system and a method of use thereof, which provide for atrial pacing by a leadless pacemaker through fixing the leadless pacemaker in a blood vessel in communication with the heart with an elastic unfoldable element.

The present invention provides a leadless pacemaker system, including:

a pacemaker fixation system including a leadless pacemaker and an elastic unfoldable element attached to the leadless pacemaker, wherein in an unfolded configuration of the elastic unfoldable element, the elastic unfoldable element fixes the leadless pacemaker at a target location in a blood vessel in communication with a heart;

a delivery system for delivering the pacemaker fixation system to the target location; and a guide for guiding the delivery system into the blood vessel.

Additionally, the target location may include a junction between a superior vena cava and a right atrium and/or a junction between an inferior vena cava and a right atrium.

Additionally, a sensing electrode and a pacing electrode may be provided on an exterior of the elastic unfoldable element.

Additionally, the elastic unfoldable element may include an elastic band, wherein one end of the elastic band is secured to the leadless pacemaker, and the other end of the elastic band defines a spiral or involute centered at a center or axis of the leadless pacemaker when the elastic band is in the unfolded configuration, and wherein the elastic band in the unfolded configuration has a maximum outer diameter greater than an inner diameter of the blood vessel at the target location.

In some embodiments, the elastic band may be ribbon-like elastic band, and at least two ribbon-like elastic bands may be provided on the leadless pacemaker and spaced apart from one another in the direction in which the blood vessel extends.

In some embodiments, the elastic band may be roll-shaped.

Additionally, the delivery system may include a module for folding the unfoldable element and a stopping device for the pacemaker fixation system, the module for folding the unfoldable element configured to fold or unfold the elastic unfoldable element so as to bring the elastic unfoldable element into a folded or unfolded configuration, the stopping device for the pacemaker fixation system configured to prevent the pacemaker fixation system from moving during retrieval of the module for folding the unfoldable element, so that the pacemaker fixation system is fixed at the target location.

Additionally, the module for folding the unfoldable element may include a loading sheath, a loading handle, a positioning sheath and a positioning handle, the loading sheath coupled to one end of the loading handle, the positioning sheath coupled to one end of the positioning handle, the positioning sheath disposed within the loading sheath so as to be movable along an axial direction of the loading sheath, the loading sheath provided with a cutout in an end portion thereof distal from the loading handle, the cutout having one edge interposed between the elastic band and the leadless pacemaker, the leadless pacemaker having one portion that is proximal to the loading handle and complementary in shape and size to, and engaged with, an end portion of the positioning sheath distal from the positioning handle, the leadless pacemaker rotatable with the positioning sheath.

Additionally, the leadless pacemaker may be provided with a fixing pole arranged along an axial direction of the leadless pacemaker, and wherein an end portion of the fixing pole proximal to the positioning sheath is coupled to an end portion of the positioning sheath distal from the positioning handle.

Additionally, the end portion of the fixing pole proximal to the positioning sheath may form a polygonal or profiled plug, while the end portion of the positioning sheath distal from the positioning handle may define a mating polygonal or profiled socket.

Additionally, the stopping device for the pacemaker fixation system may include an abutting rod and an abutting-rod handle coupled to the abutting rod, the abutting rod disposed within the positioning sheath so as to be movable axially with respect to the positioning sheath.

Additionally, the positioning sheath may extend through the loading handle into the loading sheath, with the abutting rod extending through the positioning handle into the positioning sheath, so that all of the loading sheath, the loading handle, the positioning sheath, the positioning handle, the abutting rod and the abutting-rod handle are coaxial.

Additionally, the guide may include a guiding sheath and a dilating sheath, the delivery system provided in the guiding sheath, the dilating sheath disposed within the guiding sheath so as to be movable along an axial direction of the guiding sheath, the dilating sheath configured to guide the guiding sheath and the delivery system into the blood vessel.

The present invention also provides a method of use of a leadless pacemaker system. The method includes:

guiding, by a guide, a delivery system including a pacemaker fixation system into a blood vessel in communication with a heart, the pacemaker fixation system including a leadless pacemaker and an elastic unfoldable element coupled to the leadless pacemaker;

delivering, by the delivery system, the pacemaker fixation system to a target location in the blood vessel and bringing the elastic unfoldable element into an unfolded configuration at the target location; and retrieving the guide and the delivery system, so that the leadless pacemaker is fixed at the target location.

Additionally, the guide may include a guiding sheath and a dilating sheath, the dilating sheath disposed within the guiding sheath so as to be movable along an axial direction of the guiding sheath, the dilating sheath comprising a tip protruding out of the guiding sheath from an end of the guiding sheath proximal to the heart.

Additionally, guiding, by the guide, the delivery system including the pacemaker fixation system into the blood vessel in communication with a heart includes:

delivering the guiding sheath via the dilating sheath into the blood vessel in communication with the heart;

retrieving the dilating sheath and keeping the guiding sheath in place; and loading the pacemaker fixation system into the delivery system while ensuring that the elastic unfoldable element is in a folded configuration, and guiding, by the guiding sheath, the delivery system into the blood vessel.

Additionally, the delivery system may include a module for folding the unfoldable element and a stopping device for the pacemaker fixation system, the module for folding the unfoldable element configured to fold or unfold the elastic unfoldable element so as to bring the elastic unfoldable element into the folded or unfolded configuration, the stopping device for the pacemaker fixation system configured to prevent the pacemaker fixation system from moving during retrieval of the module for folding the unfoldable element, so that the pacemaker fixation system is fixed at the target location.

Additionally, delivering, by the delivery system, the pacemaker fixation system to the target location in the blood vessel and bringing the elastic unfoldable element into the unfolded configuration at the target location may include:

bringing the elastic unfoldable element into the unfolded configuration by unfolding the elastic unfoldable element with the module for folding the unfoldable element to fix the leadless pacemaker in the blood vessel; and determining whether the elastic unfoldable element has been accurately fixed at the target location, if the elastic unfoldable element has been accurately fixed at the target location, retrieving the guide and the delivery system to make the leadless pacemaker fixed at the target location, or if the elastic unfoldable element has not been accurately fixed at the target location, bringing the elastic unfoldable element into the folded configuration by folding the elastic unfoldable element with the module for folding the unfoldable element, adjusting a position of the pacemaker fixation system along an axial direction and a radial direction of the blood vessel, and again bringing the elastic unfoldable element into the unfolded configuration by unfolding the elastic unfoldable element with the module for folding the unfoldable element to fix the leadless pacemaker in the blood vessel.

Additionally, retrieving the guide and the delivery system and keeping the leadless pacemaker fixed at the target location may include:

retrieving the module for folding the unfoldable element while immortalizing the pacemaker fixation system with the stopping device for the pacemaker fixation system so that the leadless pacemaker is alone fixed at the target location by means of the elastic unfoldable element; and retrieving all components other than the pacemaker fixation system from the blood vessel.

The present invention also provides a pacemaker fixation system, including:

a leadless pacemaker and an elastic unfoldable element attached to the leadless pacemaker, wherein in an unfolded configuration of the elastic unfoldable element, the elastic unfoldable element fixes the leadless pacemaker at a target location in a blood vessel in communication with a heart.

In the pacemaker fixation system, leadless pacemaker system and method of use thereof provided herein, the elastic unfoldable element can fix the leadless pacemaker in a blood vessel communicating with the heart, thus enabling atrial pacing of the leadless pacemaker. During implantation of the leadless pacemaker, the delivery system can adjust the position of the leadless pacemaker axially and radially with respect to the blood vessel, helping the operator easily identify the best pacing site and thus achieving an improved pacing effect of the leadless pacemaker. Further, the leadless pacemaker system can communicate in a wired or wireless manner with leadless pacemakers in different ventricles, thus enabling true leadless bi-ventricular/tri-ventricular pacing. In this way, the advanced technology, leadless pacing, can be applied to more different populations and benefit more patients.

BRIEF DESCRIPTION OF DRAWINGS

The accompanying drawings will be briefly described below so that the technical solutions provided by some embodiments of the present invention or by the prior art can be more clearly understood. Apparently, the figures set forth in the following description illustrate only some of the possible embodiments of the present invention, and those of ordinary skill in the art can obtain figures showing other embodiments from them without exerting any creative effort.

In FIGS. 1 to 12:
5—superior vena cava;
6—right atrium;
7—right ventricle;
8—inferior vena cava;
10—guide;
11—dilating sheath;
12—guiding sheath;
20—delivery system;
21—loading sheath;
22—positioning sheath;
23—abutting rod;
24—loading handle;
25—positioning handle;
26—abutting-rod handle;
27—cutout;
28—profiled hole;
30—pacemaker fixation system;
31—leadless pacemaker;
32—sensing electrode;
33—pacing electrode;
34—elastic band;
35—fixing pole.

DETAILED DESCRIPTION OF EXEMPLARY EMBODIMENTS

The leadless pacemaker system and method of use thereof proposed therein will be described in greater detail below with reference to a few specific embodiments and the accompanying drawings. Features and advantages of the present invention will be more apparent from the following detailed description, and from the appended claims. It is noted that the figures are provided in a very simplified form not necessarily presented to scale, with their only intention to facilitate convenience and clarity in explaining the disclosed embodiments.

The core idea of the present invention is to provide a leadless pacemaker system and a method of use thereof, in which an elastic unfoldable element is employed to fix a leadless pacemaker in a blood vessel communicating with the heart and allowing pacing of the heart and sensing of a signal therefrom, thereby enabling atrial pacing of the leadless pacemaker. In addition, during implantation of the leadless pacemaker, the delivery system can adjust the position of the leadless pacemaker axially and radially with respect to the blood vessel, helping the operator easily identify the best pacing site and thus achieving an improved pacing effect of the leadless pacemaker. Further, the leadless pacemaker system can build wired or wireless communication connection(s) between leadless pacemakers deployed in respective different ventricles, thus enabling leadless bi-ventricular/tri-ventricular pacing. For example, a Bluetooth communication technique may be utilized to signally connect one leadless pacemaker implanted in the right atrium to another leadless pacemaker implanted in the right ventricle so that the two leadless pacemakers can communicate and coordinate with each other to provide true leadless bi-ventricular pacing. Likewise, the Bluetooth communication technique may be utilized to achieve signal connections among leadless pacemakers respectively implanted in the right atrium, the right ventricle and the left ventricle and thus enabling the communication and coordination among the three leadless pacemakers, such that the true leadless tri-ventricular pacing can be achieved. In this way, the advanced technology, leadless pacing, can be applied to more different populations and benefit more patients.

Figure 1:
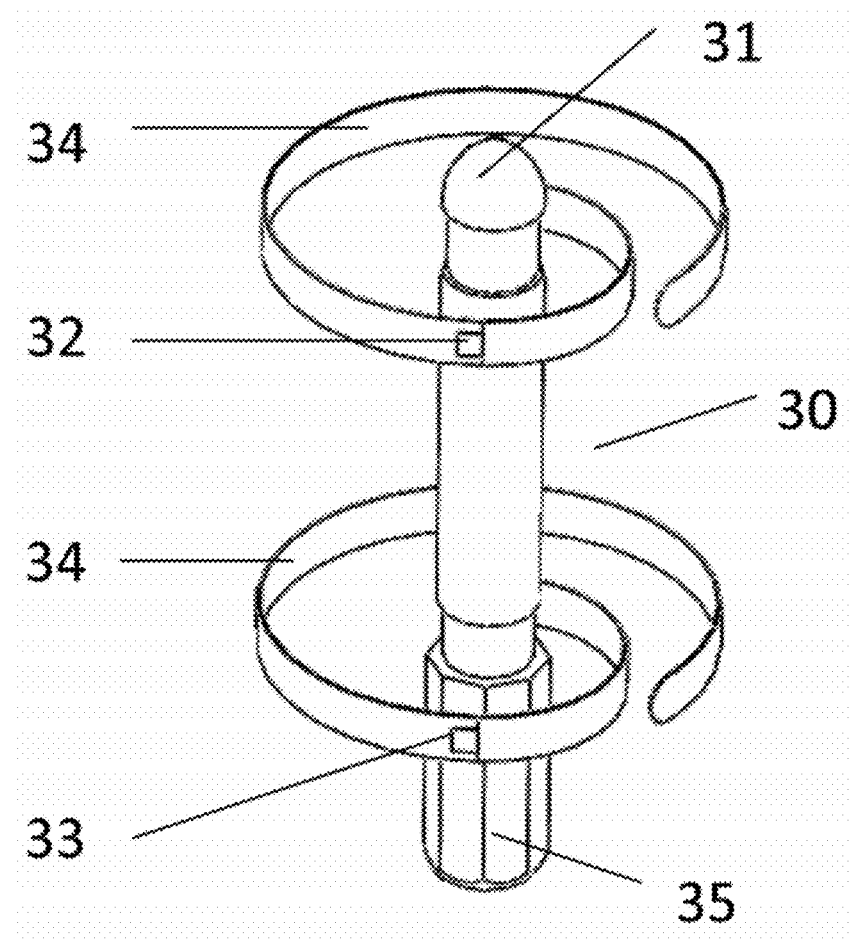
FIG. 1 is a structural schematic of a pacemaker fixation system in a leadless pacemaker system according to an embodiment of the present invention.
Figure 2:
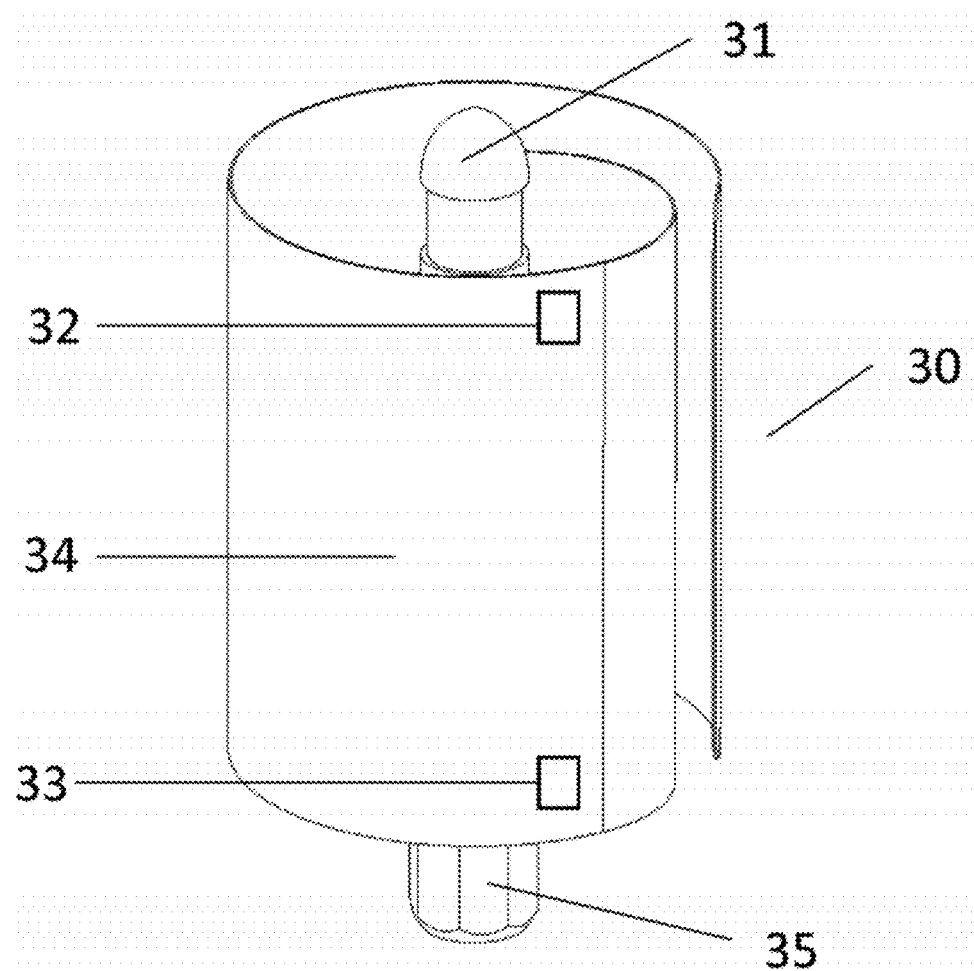
FIG. 2 is a structural schematic of another pacemaker fixation system according to an embodiment of the present invention.
Figure 3:
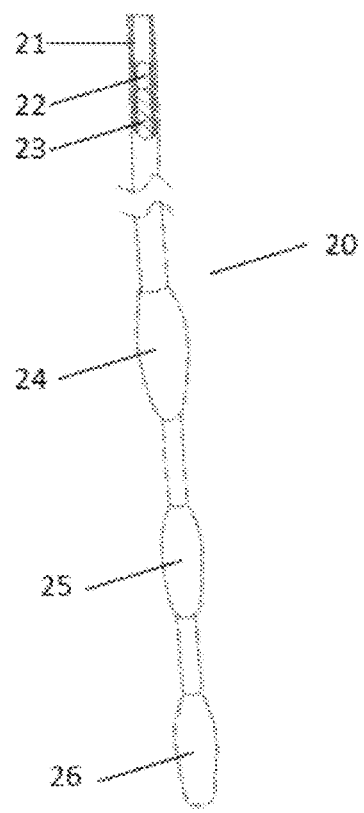
FIG. 3 is a structural schematic of a delivery system in a leadless pacemaker system according to an embodiment of the present invention.
Figure 4:
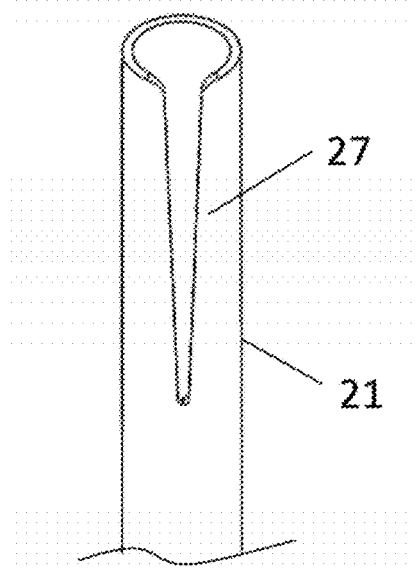
FIG. 4 is a structural schematic of a loading sheath in a delivery system according to an embodiment of the present invention.
Figure 5:
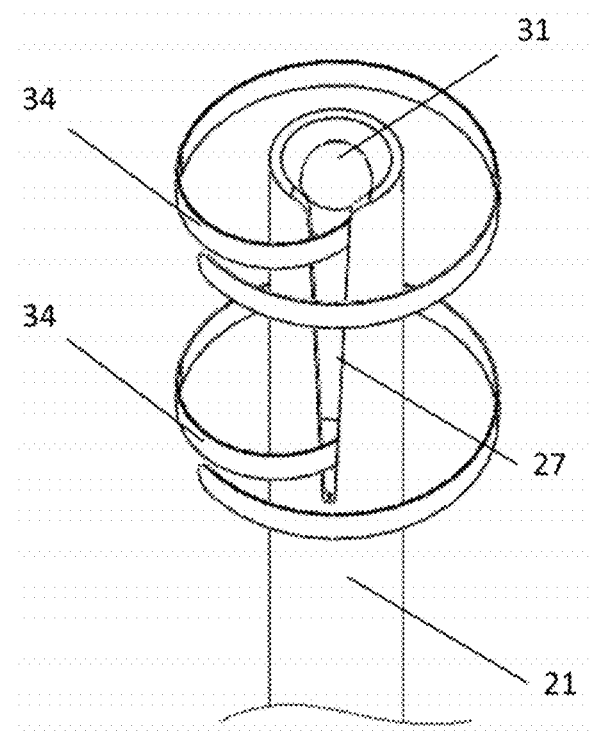
FIG. 5 is a structural schematic of an elastic band in an unfolded configuration in a pacemaker fixation system loaded in a delivery system according to an embodiment of the present invention.
Figure 6:
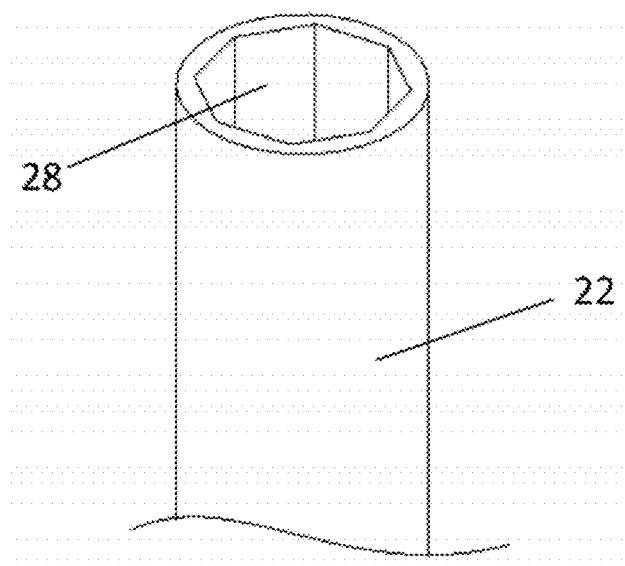
FIG. 6 is a structural schematic of a positioning sheath in a delivery system according to an embodiment of the present invention.
Figure 7:
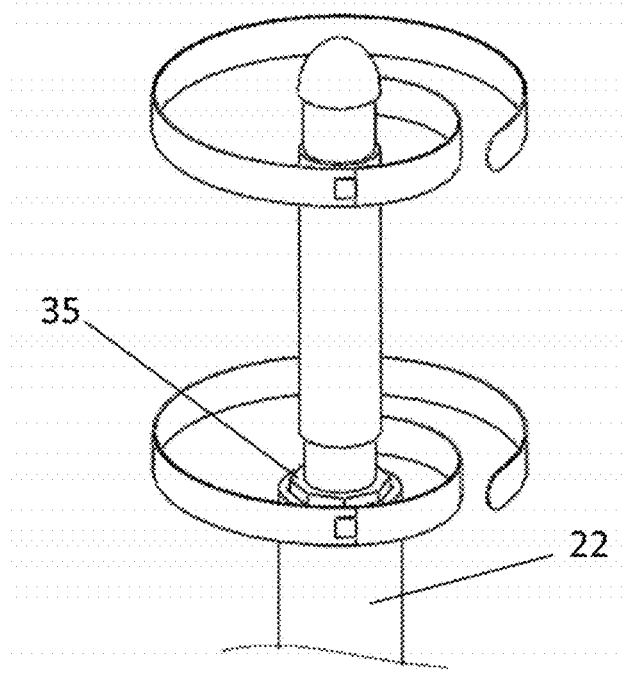
FIG. 7 is a structural schematic of a leadless pacemaker coupled to a positioning sheath according to an embodiment of the present invention.

Reference is now made to FIGS. 1 to 12. FIG. 1 is a structural schematic of a pacemaker fixation system in a leadless pacemaker system according to an embodiment of the present invention. FIG. 2 is a structural schematic of another pacemaker fixation system according to an embodiment of the present invention. FIG. 3 is a structural schematic of a delivery system in a leadless pacemaker system according to an embodiment of the present invention. FIG. 4 is a structural schematic of a loading sheath in a delivery system according to an embodiment of the present invention. FIG. 5 is a structural schematic of an elastic band in an unfolded configuration in a pacemaker fixation system loaded in a delivery system according to an embodiment of the present invention. FIG. 6 is a structural schematic of a positioning sheath in a delivery system according to an embodiment of the present invention. FIG. 7 is a structural schematic of a leadless pacemaker coupled to a positioning sheath according to an embodiment of the present invention.

Figure 8:
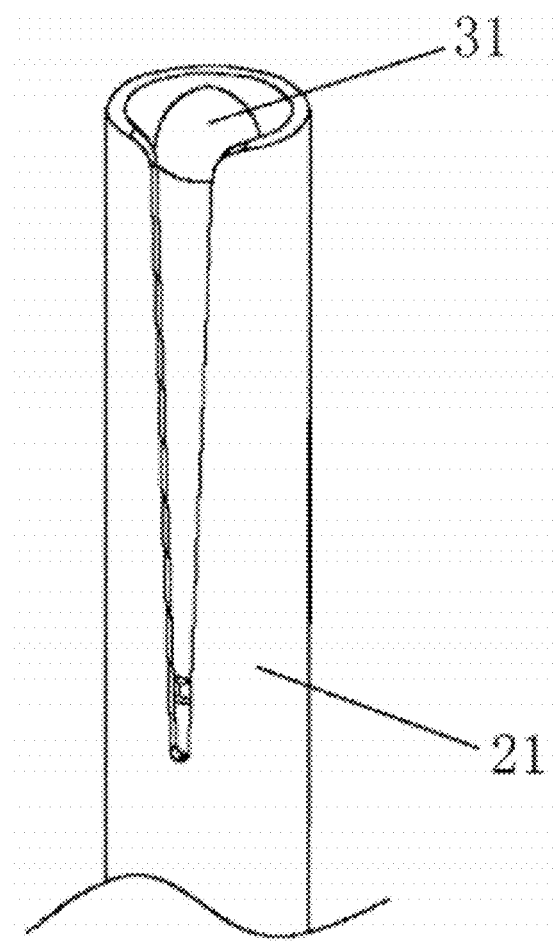
FIG. 8 is a structural schematic of an elastic band in a folded configuration in a pacemaker fixation system loaded in a delivery system according to an embodiment of the present invention.
Figure 9:
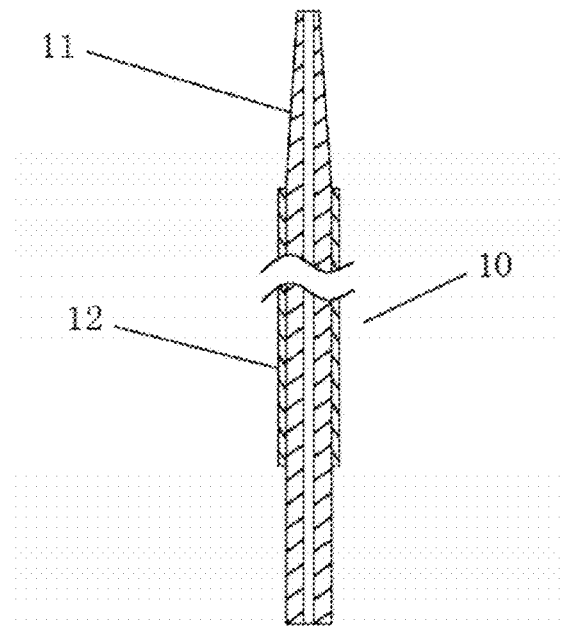
FIG. 9 is a structural schematic of a guide in a leadless pacemaker system according to an embodiment of the present invention.
Figure 10:
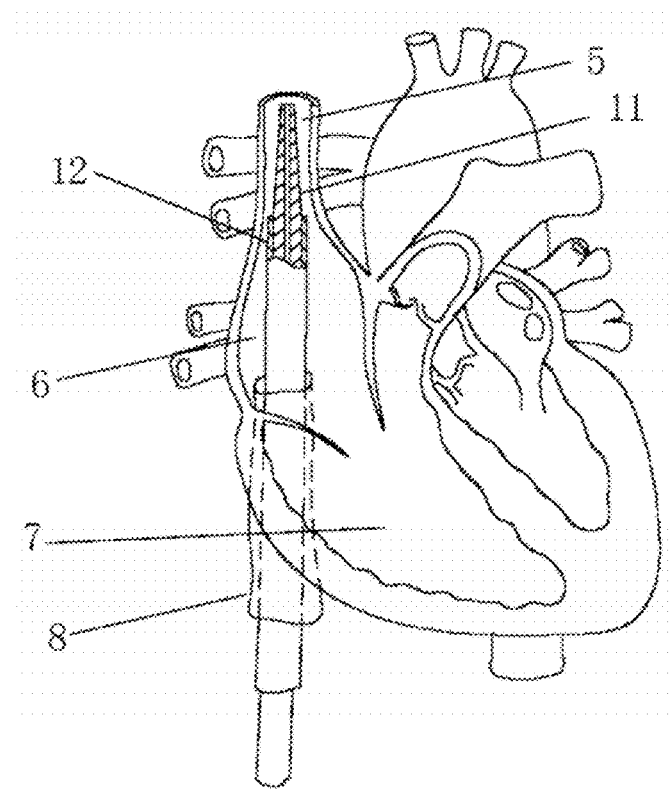
FIG. 10 is a structural schematic of a guide being introduced into the heart according to an embodiment of the present invention.
Figure 11:
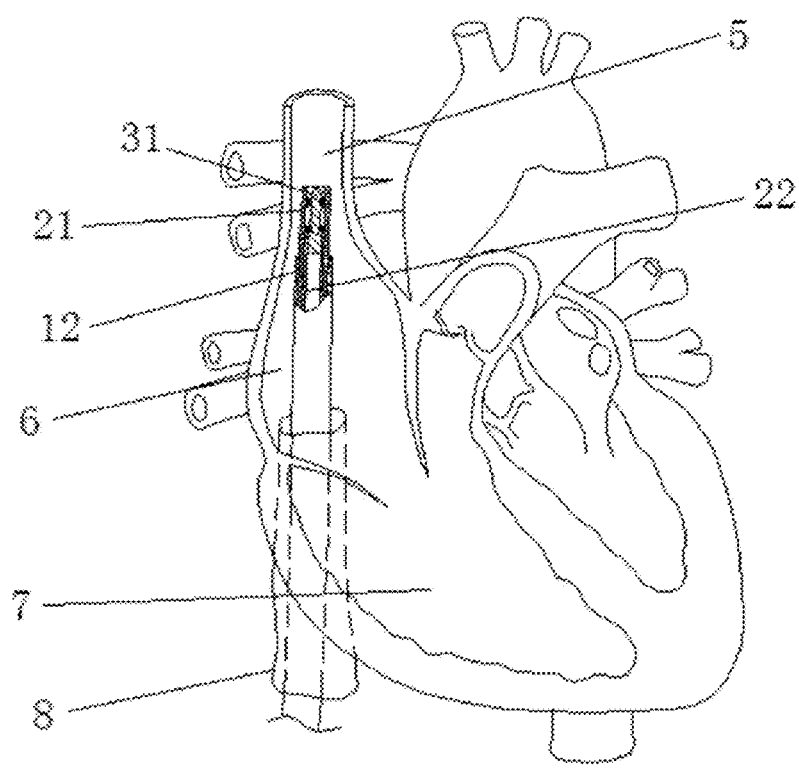
FIG. 11 is a structural schematic of a delivery system being introduced into the heart according to an embodiment of the present invention.
Figure 12:
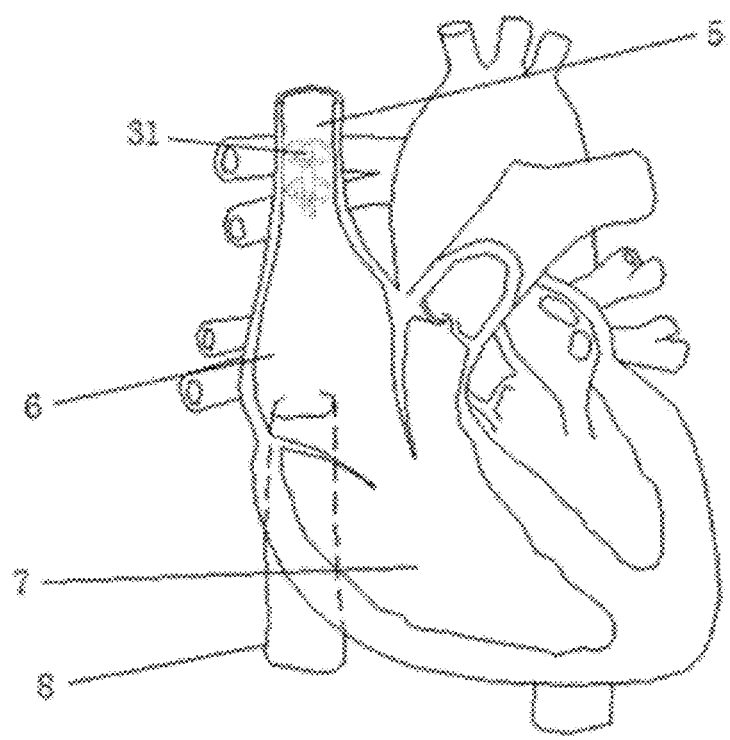
FIG. 12 is a structural schematic of a leadless pacemaker having been fixed according to an embodiment of the present invention.

FIG. 8 is a structural schematic of an elastic band in a folded configuration in a pacemaker fixation system loaded in a delivery system according to an embodiment of the present invention. FIG. 9 is a structural schematic of a guide in a leadless pacemaker system according to an embodiment of the present invention. FIG. 10 is a structural schematic of a guide being introduced into the heart according to an embodiment of the present invention. FIG. 11 is a structural schematic of a delivery system being introduced into the heart according to an embodiment of the present invention. FIG. 12 is a structural schematic of a leadless pacemaker having been fixed according to an embodiment of the present invention.

As shown in FIGS. 1, 3 and 9, in embodiments of the present invention, there is provided a leadless pacemaker system, including:

a pacemaker fixation system 30 including a leadless pacemaker 31 and an elastic unfoldable element attached to the leadless pacemaker, wherein in an unfolded configuration of the elastic unfoldable element, it fixes the leadless pacemaker 31 at a target location in a blood vessel in communication with the heart;

a delivery system 20 for delivering the pacemaker fixation system 30 to the target location; and a guide 10 for guiding the delivery system 20 into the blood vessel.

In the leadless pacemaker system according to these embodiments, the elastic unfoldable element can fix the leadless pacemaker 31 in a blood vessel communicating with the heart and allowing pacing of the heart and sensing of a signal therefrom, in particular a blood vessel located at a junction between the superior vena cava 5 and the right atrium 6 and/or a junction between the inferior vena cava 8 and the right atrium 6, thus enabling atrial pacing of the leadless pacemaker 31. During implantation of the leadless pacemaker 31, the leadless pacemaker system is also able to adjust the position of the leadless pacemaker 31 axially and radially with respect to the blood vessel by virtue of the delivery system 20, helping the operator easily identify the best pacing site and thus achieving an improved pacing effect of the leadless pacemaker 31. Further, the leadless pacemaker system can build wired or wireless communication connection(s) between leadless pacemakers deployed in respective different ventricles. This entails true leadless bi-ventricular and tri-ventricular pacing, making this advanced technology applicable to more different populations and benefit more patients.

In the present embodiment, the leadless pacemaker 31 is configured to send pacing pulses and may have a cylindrical sealed outer casing that houses electronic components supporting operation of the pacemaker, such as a pulse generator, communication electronic components, a battery and a computing processor. The architecture of such a pacemaker is common knowledge in the art and a further detailed description thereof is deemed unnecessary and omitted. It will be appreciated that, without departing from the scope of the present invention, the sealed outer casing of the leadless pacemaker 31 may also have a different shape than cylindrical, such as rectangular parallelepiped, polyhedral or the like, as long as it allows the packing function of the pacemaker.

Additionally, a sensing electrode 32 and a pacing electrode 33 may be provided on the exterior of the elastic unfoldable element, the sensing electrode 32 is configured for transmitting and receiving sense signals and the pacing electrode 33 is configured for transmitting and receiving pacing signals.

Additionally, the elastic unfoldable element may include an elastic band 34, one end of the elastic band 34 is secured to the leadless pacemaker 31 and, when in an unfolded configuration, the other end of the elastic band 34 defines a spiral centered about a center point or axis of the leadless pacemaker 31. The leadless pacemaker 31 may be rotated by an external force so that the elastic band 34 is folded on an outer surface of the leadless pacemaker 31. Upon removal of the external force, the elastic band may again unfold freely. In the unfolded configuration of the elastic band 34, a maximum outer diameter of the elastic band may be greater than an inner diameter of the blood vessel at the target location so that it is circumferentially compressed by the blood vessel wall, thereby fixing the leadless pacemaker 31 at the target location in the blood vessel.

In the present embodiment, in order to provide good fixation to the leadless pacemaker 31 while not causing damage to the blood vessel, the maximum outer diameter of the elastic band 34 in the unfolded configuration thereof is desirable to be 0.5-50 millimeters (mm) greater than the inner diameter of the blood vessel at the target location.

In the present embodiment, the elastic band 34 may have a thickness of 0.05-1 mm and fabricated from a memory metal (e.g., nitinol) sheet so that it is light in weight while providing good fixation.

It will be appreciated that, without departing from the scope of the present invention, in the unfolded configuration of the elastic band 34, the other end of the elastic band 34 may alternatively define an involute or another curve unfolded from the leadless pacemaker 31 and centered about the center point or axis of the leadless pacemaker, as long as the elastic band 34 is allowed to assume an unfolded configuration and a folded configuration.

As shown in FIG. 1, in embodiments of the present invention, the elastic band 34 may be ribbon-like and at least two such ribbon-like elastic bands 34 may be provided on the leadless pacemaker and spaced apart from each other or one another along an axial direction of the leadless pacemaker. In particular, two such elastic bands 34 may be attached respectively to proximal (close to an operator) and distal (distal from the operator) portions of the leadless pacemaker 31 in order to provide the leadless pacemaker 31 with two fixation points spaced apart by a rather large distance, which enable an even more secure fixation of the leadless pacemaker 31. In the case of such elastic band 34, the sensing electrode 32 and the pacing electrode 33 may be respectively provided on the two elastic bands 34 in order to avoid signal crosstalk between the sensing electrode 32 and the pacing electrode 33.

As shown in FIG. 2, in another embodiment, the elastic band 34 may be roll-shaped so as to provide a sufficient area for the fixation of the leadless pacemaker 31. In the case of such elastic band 34, the sensing electrode 32 and the pacing electrode 33 may be both provided on the roll-shaped elastic band and spaced apart from each other along the axial direction of the leadless pacemaker in order to avoid signal crosstalk between the sensing electrode 32 and the pacing electrode 33.

Additionally, as shown in FIG. 3, the delivery system may include a module for folding the unfoldable element and a stopping device for the pacemaker fixation system. The module for folding the unfoldable element may be configured to fold or unfold the elastic unfoldable element (i.e., the elastic band 34) so as to bring the elastic unfoldable element into the folded or unfolded configuration. The stopping device for the pacemaker fixation system may be configured to prevent dislocation of the pacemaker fixation system from the target location during retrieval of the module for folding the unfoldable element. In the unfolded configuration of the elastic unfoldable element, the operator can perform a program-controlled test to verify its pacing and sensing electrical parameters. If the measured parameters are unsatisfactory due to deployment at a non-ideal pacing site, the operator may again fold the elastic band 34 by operating the module for folding the unfoldable element and then adjust the position of the leadless pacemaker 31 in the blood vessel and hence those of the sensing electrode 32 and the pacing electrode 33 on the inner blood vessel wall through axially or radially displacing or circumferentially rotating the pacemaker fixation system 30 with the aid of the delivery system, followed by unfolding the elastic band 34 by manipulating the module for folding the unfoldable element and performing another test on pacing and sensing electrical parameters. This process can be repeated until desired electrical parameters are obtained.

Further, as shown in FIGS. 3 to 8, the module for folding the unfoldable element may include a loading sheath 21, a loading handle 24, a positioning sheath 22 and a positioning handle 25. The loading handle 24 is coupled to one end of the loading sheath 21 and the positioning handle 25 is coupled to one end of the positioning sheath 22. The positioning sheath 22 may be disposed within the loading sheath 21 so that it is movable along an axial direction of the loading sheath 21. A slot 27 may be provided in an end portion of the loading sheath 21 distal from the loading handle 24. In order to deliver the pacemaker fixation system 30 by the delivery system 20, the pacemaker fixation system 30 may be loaded in the delivery system 20 in such a manner that one edge of the slot 27 is interposed between the elastic band 34 and the leadless pacemaker 31. An end portion of the leadless pacemaker 31 proximal to the loading handle 24 may be complementary in shape and size to, and engaged with, an end portion of the positioning sheath 22 distal from the positioning handle 25, and the leadless pacemaker may rotate with the positioning sheath 22. As shown in FIGS. 5 and 8, from the configuration of FIG. 5, the elastic band 34 can be completely folded, when the operator holds the loading handle 24 with one hand and turns the positioning handle 25 clockwise with the other hand. The configuration of folding is shown in FIG. 8, in the configuration of the elastic band 34 completely folded and received in the distal end portion of the loading sheath 21, the elastic band 34 can be unfolded when the positioning handle 25 is turned counterclockwise.

Additionally, as shown in FIGS. 1, 2 and 7, the leadless pacemaker 31 may include a fixing pole 35 extending along the axial direction of the leadless pacemaker. An end portion of the fixing pole 35 proximal to the positioning sheath 22 may be coupled to an end portion of the positioning sheath 22 distal from the positioning handle 25. With the fixing pole 35, the leadless pacemaker 31 does not need to be coupled by itself to the positioning sheath 22, reducing the impact of movement on the leadless pacemaker 31 and increasing the stability of the leadless pacemaker 31.

Additionally, as shown in FIG. 6, the end portion of the fixing pole 35 proximal to the positioning sheath 22 may form a profiled plug, while the end portion of the positioning sheath 22 distal from the positioning handle 25 may define a mating profiled socket 28. This design prevents relative rotation between the leadless pacemaker 31 and the positioning sheath 22 when the positioning sheath 22 is driving axial or radial movement of the pacemaker fixation system 30 with respect to the blood vessel, ensuring positioning accuracy of the leadless pacemaker 31.

It will be appreciated that, without departing from the scope of the present invention, the profiled shape of the end portion and hole 28 may be replaced with any suitable polyhedral or other regular or irregular shape with corner ridge(s), as long as it can prevent relative rotation between the leadless pacemaker 31 and the positioning sheath 22.

Additionally, as shown in FIG. 3, the stopping device for the pacemaker fixation system may include an abutting rod 23 and an abutting-rod handle 26 coupled to the abutting rod. The abutting rod 23 may be housed in the positioning sheath 22 so as to be moveable axially in the positioning sheath 22.

Additionally, the positioning sheath 22 may extend through the loading handle 24 into the loading sheath 21, while the abutting rod 23 may extend through the positioning handle 25 into the positioning sheath 22. Further, all of the loading sheath 21, the loading handle 24, the positioning sheath 22, the positioning handle 25, the abutting rod 23 and the abutting-rod handle 26 may be coaxial. This design can effectively reduce the spatial footprint of the leadless pacemaker system, leaving more room for the operator's operation, which is helpful in improving the operator's operational accuracy.

In order to retrieve the module for folding the unfoldable element from the patient's body, the operator may insert a distal (distal from the abutting-rod handle 26) end of the abutting rod 23 into a proximal (close to the positioning handle 25) end of the positioning sheath 22 and advance the abutting rod 23 toward the distal (distal from the positioning handle 25) end of the positioning sheath 22 until the distal end of the abutting rod 23 comes into contact with the fixing pole 35. After that, with one hand holding the abutting-rod handle 26, the operator may grip and proximally (close to the operator) retract the loading handle 24 and the positioning handle 25 successively.

Additionally, as shown in FIG. 9, the guide 10 may include a guiding sheath 12 and a dilating sheath 11. The dilating sheath 11 is disposed in the guiding sheath 12 so as to be able to move axially with respect to the guiding sheath 12. The dilating sheath 11 may have a tip protruding out of the guiding sheath 12 from an end thereof proximal to the heart. This tip of the dilating sheath 11 may be configured to widen a blood vessel in the heart to allow smooth entry of the guiding sheath 12 into the blood vessel.

In the present embodiment, except for the electronic components arranged within the leadless pacemaker 31, each of the other components may be made of a polymer in order to minimize possible damage that they may cause to the patient's body. Ideally, without departing from the scope of the present invention, those components may also be each made of any other suitable material that is not harmful to human health, as long as it can minimize possible damage to the patient's body.

In embodiments of the present invention, there is also provided a pacemaker fixation system including a leadless pacemaker and an elastic unfoldable element coupled thereto. In an unfolded configuration of the elastic unfoldable element, it fixes the leadless pacemaker at a target location in a blood vessel in communication with the heart.

The pacemaker fixation system is identical in structure to those described above, and will not be described in detail again here.

As shown in FIGS. 1 to 12, in embodiments of the present invention, there is also provided a method of use of a leadless pacemaker system, including the steps of:

1) guiding, by a guide 10, a delivery system 20 including a pacemaker fixation system 30 into a blood vessel in communication with the heart, the pacemaker fixation system 30 including a leadless pacemaker 31 and an elastic unfoldable element coupled to the leadless pacemaker;

2) delivering, by the delivery system 20, the pacemaker fixation system 30 to a target location in the blood vessel and bringing the elastic unfoldable element into an unfolded configuration at the target location; and 3) retrieving the guide and the delivery system, leaving the leadless pacemaker fixed at the target location.

Additionally, the guide may include a guiding sheath and a dilating sheath, the dilating sheath disposed within the guiding sheath so as to be movable axially with respect to the guiding sheath, the dilating sheath having a tip protruding out of the guiding sheath from an end thereof proximal to the heart. Specifically, step 1 may include the steps of:

1A) delivering the guiding sheath 12 via the dilating sheath 11 into the blood vessel in communication with the heart;

1B) retrieving the dilating sheath 11 within the guiding sheath 12, with the guiding sheath 12 remaining as delivered; and 1C) loading the pacemaker fixation system 30 into the delivery system 20 while ensuring that the elastic unfoldable element therein is in a folded configuration, and guiding, via the guiding sheath 12, the delivery system 20 into the blood vessel.

Additionally, the delivery system may include a module for folding the unfoldable element and a stopping device for the pacemaker fixation system, the module for folding the unfoldable element configured to fold or unfold the elastic unfoldable element so as to bring it into the folded or unfolded configuration, the stopping device for the pacemaker fixation system configured to prevent the pacemaker fixation system from moving with retrieval of the module for folding the unfoldable element and thus leave it fixed at the target location. Specifically, step 2 may include the steps of:

2A) bringing the elastic unfoldable element into the unfolded configuration by unfolding it with the module for folding the unfoldable element, resulting in fixation of the leadless pacemaker 31 in the blood vessel; and 2B) determining whether the elastic unfoldable element has been accurately fixed at the target location, followed by performing, for another time, step 3 in case of the determination being positive or step 2C in case of the determination being negative:

2C) bringing the elastic unfoldable element into the folded configuration by folding it with the module for folding the unfoldable element, adjusting the position of the pacemaker fixation system 30 axially and radially with respect to the blood vessel, and again perform step 2A.

Additionally, step 3 may include the steps of:

3A) retrieving the module for folding the unfoldable element while immortalizing the pacemaker fixation system with the stopping device for the pacemaker fixation system so that the leadless pacemaker 31 is alone fixed at the target location by virtue of the elastic unfoldable element; and 3B) retrieving all the components from the blood vessel except the pacemaker fixation system 30.

The method of use of a leadless pacemaker system will be described in further detail below in the context of fixing the leadless pacemaker 31 at a junction between the superior vena cava 5 and the right atrium 6 as an example.

Referring to FIGS. 1 to 12, prior to the implantation of the leadless pacemaker 31, the positioning sheath 22 may be inserted into the inside of the loading sheath 21, and the pacemaker fixation system 30 may be placed into the inside of the loading sheath 21 in such a manner that the elastic band 34 is inserted through the slot 27. The positioning handle 25 may be then rotated so that the elastic band 34 is folded, as shown in FIG. 8.

During the implantation, at first, the dilating sheath 11 and the guiding sheath 12 may be delivered from the femoral vein through the inferior vena cava 8 to the location as shown 10, and the dilating sheath 11 may be then retrieved, with the guiding sheath 12 remaining at the location. In the configuration of FIG. 8, the loading sheath 21 may be inserted, at a distal (distal from the loading handle 24) end thereof, into the guiding sheath 12 from a proximal end thereof and advanced to a location around the superior vena cava 5, as shown in FIG. 11. Subsequently, the operator can hold the loading handle 24 with one hand and turn the positioning handle 25 counterclockwise so as to unfold the elastic band 34, bringing the sensing electrode 32 and the pacing electrode 33 into contact with an inner wall of the superior vena cava 5. At this point, a program-controlled test may be performed to verify pacing and sensing electrical parameters. If the obtained pacing and sensing electrical parameters are unsatisfactory due to deployment at a suboptimal pacing site, the elastic band 34 can be unfolded and retracted back into the loading sheath 21 by rotating the positioning handle 25 clockwise, and the position of the leadless pacemaker 31 in the superior vena cava 5 can be tuned by moving both the loading sheath 21 and the positioning sheath 22 axially or radially with respect to the superior vena cava 5 or rotating them circumferentially. After that, the elastic band 34 can be unfolded in the same way as described above at the new location, again bringing the sensing electrode 32 and the pacing electrode 33 into contact with a new location of the inner wall of the superior vena cava 5. Another test may be then performed to obtain new pacing and sensing electrical parameters. This process may be repeated until desired electrical parameters are obtained. Afterward, the abutting rod 23 may be inserted, at a distal end thereof, into the positioning sheath 22 from a proximal end thereof and advanced toward a distal end of the positioning sheath 22 until the distal end of the abutting rod 23 comes into contact with the fixing pole 35. At this point, the operator can hold the abutting-rod handle 26 with one hand and then successively gripping and proximally retracting the loading handle 24 and the positioning handle 25 with the other hand, thus retrieving the loading sheath 21 and the positioning sheath 22 from the superior vena cava 5. At last, all the components except the pacemaker fixation system 30 may be removed from the patient's body through the femoral vein, leaving the leadless pacemaker 31 fixed at the target location in the superior vena cava 5, as shown in FIG. 12.

Alternatively, the leadless pacemaker 31 may be fixed at a junction between the inferior vena cava 8 and the right atrium in a similar manner, and this is intended to be also included within the scope of the present invention.

It is apparent that those skilled in the art can make various modifications and variations to the present invention without departing from the spirit and scope thereof. Accordingly, the invention is intended to embrace all such modifications and variations if they fall within the scope of the appended claims and equivalents thereof.

What is claimed is:
1. A leadless pacemaker system, comprising:
a pacemaker fixation system comprising a leadless pacemaker and an elastic unfoldable element attached to the leadless pacemaker, wherein in an unfolded configuration of the elastic unfoldable element, the elastic unfoldable element fixes the leadless pacemaker at a target location in a blood vessel in communication with a heart;

a delivery system for delivering the pacemaker fixation system to the target location; and a guide for guiding the delivery system into the blood vessel;

wherein the elastic unfoldable element comprises an elastic band, one end of the elastic band is secured to the leadless pacemaker, and the other end of the elastic band defines a structure centered at a center or axis of the leadless pacemaker when the elastic band is in the unfolded configuration, wherein the delivery system comprises a module for folding the unfoldable element, the module for folding the unfoldable element comprising a loading sheath and a loading handle, the loading sheath coupled to one end of the loading handle, the loading sheath provided with a cutout in an end portion thereof distal from the loading handle, the cutout having one edge interposed between the elastic band and the leadless pacemaker.

2. The leadless pacemaker system of claim 1, wherein the target location comprises a junction between a superior vena cava and a right atrium and/or a junction between an inferior vena cava and a right atrium.

3. The leadless pacemaker system of claim 1, wherein a sensing electrode and a pacing electrode are provided on an exterior of the elastic unfoldable element, and wherein in the unfolded configuration of the elastic unfoldable element, both the sensing electrode and the pacing electrode are brought into contact with an inner wall of the blood vessel.

4. The leadless pacemaker system of claim 1, wherein the other end of the elastic band defines a spiral or involute centered at the center or axis of the leadless pacemaker when the elastic band is in the unfolded configuration, and wherein the elastic band in the unfolded configuration has a maximum outer diameter greater than an inner diameter of the blood vessel at the target location.

5. The leadless pacemaker system of claim 4, wherein the elastic band is a ribbon-like elastic band, and at least two ribbon-like elastic bands are provided on the leadless pacemaker and spaced apart from one another along an axial direction of the leadless pacemaker.

6. The leadless pacemaker system of claim 4, wherein the elastic band is roll-shaped.

7. The leadless pacemaker system of claim 1, wherein the delivery system further comprises a stopping device for the pacemaker fixation system, the module for folding the unfoldable element configured to fold or unfold the elastic unfoldable element so as to bring the elastic unfoldable element into a folded or unfolded configuration, the stopping device for the pacemaker fixation system configured to prevent the pacemaker fixation system from moving during retrieval of the module for folding the unfoldable element, so that the pacemaker fixation system is fixed at the target location.

8. The leadless pacemaker system of claim 7, wherein the stopping device for the pacemaker fixation system comprises an abutting rod and an abutting-rod handle coupled to the abutting rod, the abutting rod disposed within the positioning sheath so as to be movable axially with respect to the positioning sheath.

9. The leadless pacemaker system of claim 8, wherein the positioning sheath extends through the loading handle into the loading sheath, with the abutting rod extending through the positioning handle into the positioning sheath, so that all of the loading sheath, the loading handle, the positioning sheath, the positioning handle, the abutting rod and the abutting-rod handle are coaxial.

10. The leadless pacemaker system of claim 1, wherein the module for folding the unfoldable element further comprises a positioning sheath and a positioning handle, the positioning sheath coupled to one end of the positioning handle, the positioning sheath disposed within the loading sheath so as to be movable along an axial direction of the loading sheath, the leadless pacemaker having one portion that is proximal to the loading handle and complementary in shape and size to, and engaged with, an end portion of the positioning sheath distal from the positioning handle, the leadless pacemaker rotatable with the positioning sheath.

11. The leadless pacemaker system of claim 10, wherein one end of the leadless pacemaker is coupled to a fixing pole arranged along an axial direction of the leadless pacemaker, and wherein an end portion of the fixing pole proximal to the positioning sheath is coupled to an end portion of the positioning sheath distal from the positioning handle.

12. The leadless pacemaker system of claim 11, wherein the end portion of the fixing pole proximal to the positioning sheath forms a polygonal or profiled plug, while the end portion of the positioning sheath distal from the positioning handle defines a mating polygonal or profiled socket.

13. The leadless pacemaker system of claim 1, wherein the guide comprises a guiding sheath and a dilating sheath, the delivery system provided in the guiding sheath, the dilating sheath disposed within the guiding sheath so as to be movable along an axial direction of the guiding sheath, the dilating sheath configured to guide the guiding sheath and the delivery system into the blood vessel.

14. A method of use of a leadless pacemaker system, comprising:

guiding, by a guide, a delivery system comprising a pacemaker fixation system into a blood vessel in communication with a heart, the pacemaker fixation system comprising a leadless pacemaker and an elastic unfoldable element coupled to the leadless pacemaker;

delivering, by the delivery system, the pacemaker fixation system to a target location in the blood vessel and bringing the elastic unfoldable element into an unfolded configuration at the target location; and retrieving the guide and the delivery system, so that the leadless pacemaker is fixed at the target location;

wherein the elastic unfoldable element comprises an elastic band, one end of the elastic band is secured to the leadless pacemaker, and the other end of the elastic band defines a structure centered at a center or axis of the leadless pacemaker when the elastic band is in the unfolded configuration, wherein the delivery system comprises a module for folding the unfoldable element, the module for folding the unfoldable element comprising a loading sheath and a loading handle, the loading sheath coupled to one end of the loading handle, the loading sheath provided with a cutout in an end portion thereof distal from the loading handle, the cutout having one edge interposed between the elastic band and the leadless pacemaker.

15. The method of use of a leadless pacemaker system of claim 14, wherein the guide comprises a guiding sheath and a dilating sheath, the dilating sheath disposed within the guiding sheath so as to be movable along an axial direction of the guiding sheath, the dilating sheath comprising a tip protruding out of the guiding sheath from an end of the guiding sheath proximal to the heart.

16. The method of use of a leadless pacemaker system of claim 15, wherein guiding, by the guide, the delivery system comprising the pacemaker fixation system into the blood vessel in communication with a heart comprises:

delivering the guiding sheath via the dilating sheath into the blood vessel in communication with the heart;

retrieving the dilating sheath and keeping the guiding sheath in place; and loading the pacemaker fixation system into the delivery system while ensuring that the elastic unfoldable element is in a folded configuration, and guiding, by the guiding sheath, the delivery system into the blood vessel.

17. The method of use of a leadless pacemaker system of claim 14, wherein the delivery system further comprises a stopping device for the pacemaker fixation system, the module for folding the unfoldable element configured to fold or unfold the elastic unfoldable element so as to bring the elastic unfoldable element into the folded or unfolded configuration, the stopping device for the pacemaker fixation system configured to prevent the pacemaker fixation system from moving during retrieval of the module for folding the unfoldable element, so that the pacemaker fixation system is fixed at the target location.

18. The method of use of a leadless pacemaker system of claim 17, wherein delivering, by the delivery system, the pacemaker fixation system to the target location in the blood vessel and bringing the elastic unfoldable element into the unfolded configuration at the target location comprises:

bringing the elastic unfoldable element into the unfolded configuration by unfolding the elastic unfoldable element with the module for folding the unfoldable element to fix the leadless pacemaker in the blood vessel; and determining whether the elastic unfoldable element has been accurately fixed at the target location, if the elastic unfoldable element has been accurately fixed at the target location, retrieving the guide and the delivery system to make the leadless pacemaker fixed at the target location, or if the elastic unfoldable element has not been accurately fixed at the target location, bringing the elastic unfoldable element into the folded configuration by folding the elastic unfoldable element with the module for folding the unfoldable element, adjusting a position of the pacemaker fixation system along an axial direction and a radial direction of the blood vessel, and again bringing the elastic unfoldable element into the unfolded configuration by unfolding the elastic unfoldable element with the module for folding the unfoldable element to fix the leadless pacemaker in the blood vessel.

19. The method of use of a leadless pacemaker system of claim 17, wherein retrieving the guide and the delivery system and keeping the leadless pacemaker fixed at the target location comprises:

retrieving the module for folding the unfoldable element while immobilizing the pacemaker fixation system with the stopping device for the pacemaker fixation system so that the leadless pacemaker is independently fixed at the target location by means of the elastic unfoldable element; and retrieving all components other than the pacemaker fixation system from the blood vessel.

\* \* \* \* \*